US00PP24624P2

(12) United States Plant Patent
Bremner

(10) Patent No.: US PP24,624 P2
(45) Date of Patent: Jul. 8, 2014

(54) ***GERANIUM* PLANT NAMED 'BREMDREAM'**

(50) Latin Name: *Geranium traversii×oxonianum*
Varietal Denomination: Bremdream

(71) Applicant: Alan Bremner, Orkney (GB)

(72) Inventor: Alan Bremner, Orkney (GB)

( * ) Notice: Subject to any disclaimer, the term of this patent is extended or adjusted under 35 U.S.C. 154(b) by 118 days.

(21) Appl. No.: 13/573,684

(22) Filed: Oct. 3, 2012

(51) Int. Cl.
*A01H 5/00* (2006.01)

(52) U.S. Cl.
USPC ..... Plt./324

(58) Field of Classification Search
USPC ..... Plt./324
See application file for complete search history.

*Primary Examiner* — Susan McCormick Ewoldt
(74) *Attorney, Agent, or Firm* — Penny J. Aguirre

(57) ABSTRACT

A new cultivar of *Geranium*, 'Bremdream', characterized by its long blooming season; blooming from early May to late September in the United Kingdom, its large flowers that are about 2.9 cm in diameter, and its flowers that are light pink with purple veining and change to medium pink with purple veining as they mature creating a multiple color effect when in bloom.

2 Drawing Sheets

Botanical classification: *Geranium traversii×oxonianum.*
Cultivar designation: 'Bremdream'.

BACKGROUND OF THE INVENTION

The present invention relates to a new and distinct cultivar of *Geranium* plant, botanically a hybrid of *Geranium Geranium traversii×oxonianum*, known as *Geranium* 'Bremdream' and will be referred to hereafter by its cultivar name, 'Bremdream'.

The new variety of *Geranium*, 'Bremdream', resulted from a controlled crosse made by the Inventor in Orkney, United Kingdom in 1992 between *Geranium traversii* 'TWVA' (not patented) as the female parent and *Geranium oxonianum* 'Wageningen' (not patented) as the male parent. 'Bremdream' was selected as a single unique plant in June of 1996

Asexual reproduction of the new cultivar was first accomplished by vegetative stem cuttings in Orkney, United Kingdom in 1996 by the Inventor. Propagation has determined that the characteristics of this cultivar are stable and are reproduced true to type in successive generations.

SUMMARY OF THE INVENTION

The following traits have been repeatedly observed and represent the characteristics of 'Bremdream'. These attributes in combination distinguish 'Bremdream' as a new and distinct cultivar of *Geranium.*

1. 'Bremdream' exhibits a long blooming season; blooming from early May to late September in the United Kingdom.
2. 'Bremdream' exhibits large flowers about 2.9 cm in diameter.
3. 'Bremdream' has flowers that are light pink with purple veining and change to medium pink with purple veining as they mature creating a multiple color effect when in bloom.

The female parent of 'Bremdream', *Geranium traversii* 'TWVA' differs from 'Bremdream' in having lighter green foliage, a less vigorous growth habit, and a much shorter flowering period. The male parent of 'Bremdream', *Geranium oxonianum* 'Wageningen' differs from 'Bremdream' in having much smaller flowers, darker pink flowers, and a much shorter flowering period. The new cultivar, 'Bremdream' can be most closely compared to *Geranium* 'Mavis Simpson' (not patented). 'Mavis Simpson' differs from 'Bremdream' in having darker pink flowers that do not change color as the flower matures and in having a much shorter bloom period.

BRIEF DESCRIPTION OF THE DRAWING

The accompanying colored photographs illustrate the overall appearance and distinct characteristics of the new *Geranium*. The following is a detailed description of 24 month-old plants as grown outdoors in 10-liter pots in Boskoop, The Netherlands The photograph in FIG. 1 is a view of a plant of 'Bremdream' in bloom.

The photograph in FIG. 2 is of a close- up view of a newly opened flower of 'Bremdream'.

Figure 1:
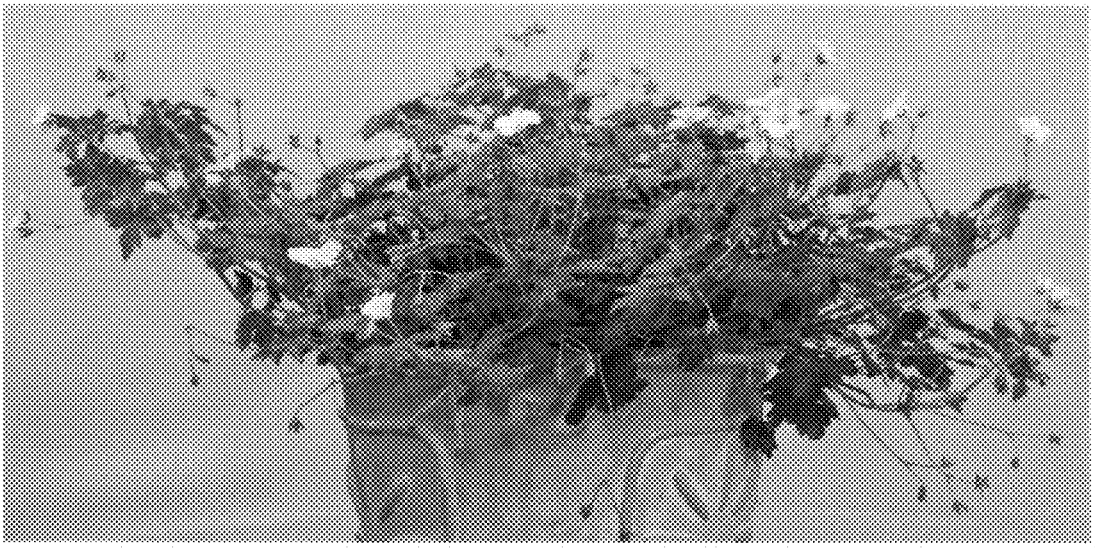
Figure 2:
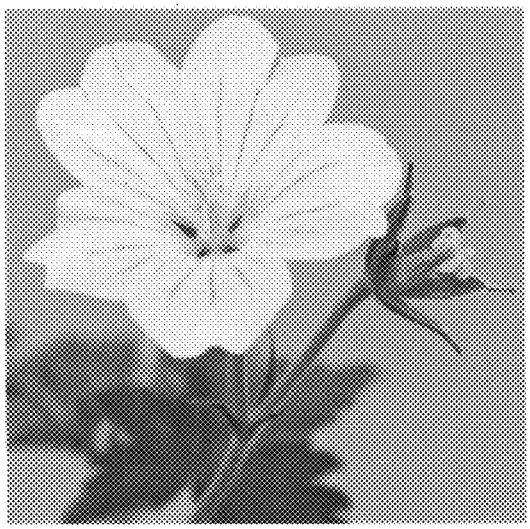
Figure 3:
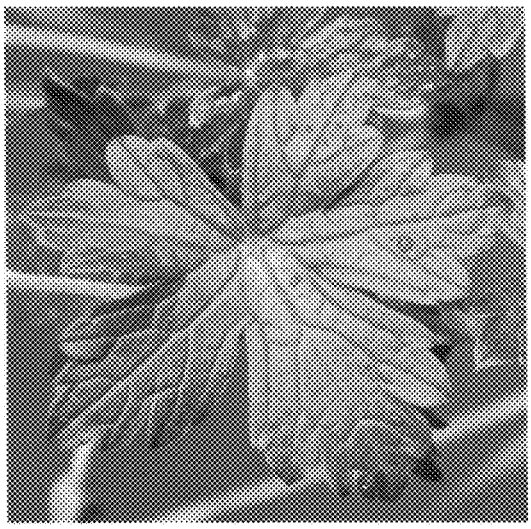

The photograph in FIG. 3 provides a close-up view of a leaf of 'Bremdream'.

Figure 4:
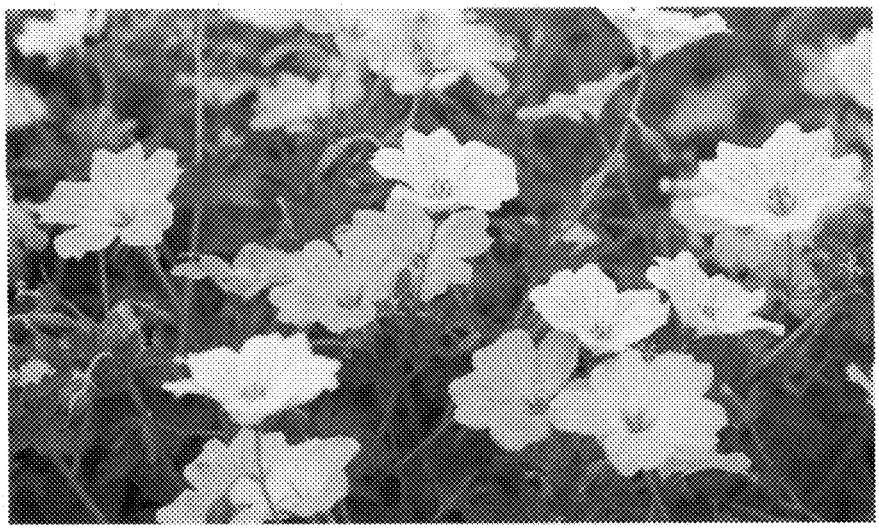

The photograph in FIG. 4 provides a view of the change in flower coloration of 'Bremdream'. The colors in the photographs are as close as possible with the photographic and printing technology utilized and the color values cited in the detailed botanical description accurately describe the colors of the new *Geranium.*

DETAILED BOTANICAL DESCRIPTION OF THE PLANT

The following is a detailed description of 24 month-old plants as grown outdoors in 10-liter pots in Orkney, United Kingdom. Plants were grown under average day temperatures of 15° C. to 28° C. and average night temperatures of 6° C. to 15° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—Continuosly from early May to late September in The Netherlands.

*Plant habit*.—Herbaceous perennial with broadly spreading growth habit.

*Height and spread*.—Reaches about 27.2 cm in height and about 73.5 cm in spread.

*Cold hardiness*.—At least to U.S.D.A. Zone 5.

*Heat tolerance*.—At least tolerant to temperature up to 35° C.

*Diseases and pests*.—No particular susceptibility or resistance to pests or diseases.

*Root description*.—Fibrous roots extending from stout rootstock.

*Branching habit*.—Freely branched, average of 40 lateral branches.

Growth and propagation:

*Growth rate*.—Moderate to vigorous.

*Propagation*.—Vegetative stem cuttings.

Stem description:

*Stem size*.—Average of 26.4 cm in length and 3 mm in width.

*Stem shape*.—Rounded.

*Stem strength*.—Moderately strong.

*Stem color*.—Both surfaces 144A to 144B, heavily tinged with 184B.

*Stem surface*.—Both surfaces slightly glossy and densely covered with short adpressed hairs average of 1 mm in length and NN155D in color.

*Internode length*.—Average of 10.7 cm.

Foliage description:

*Leaf shape*.—Orbicular to reniform (overall shape), palmately cleft to parted with an average of five lobes.

*Leaf division*.—Single.

*Leaf base*.—Hastate and slightly overlapping.

*Leaf apex*.—Broadly acute.

*Leaf venation*.—Palmate, 144A in color on upper surface and 138B on lower surface.

*Leaf margins*.—Palmately cleft into an average of five lobes, margins of lobes serrate.

*Leaf attachment*.—Petiolate.

*Leaf arrangement*.—Opposite.

*Leaf surface*.—Upper surface glossy and moderately covered with short and soft adpressed hairs average of 0.7 mm in length and NN155D in color, lower surface dull and moderately covered with short soft hairs becoming more densely covered on the main and secondary veins average length 1 mm length and NN155D in color.

*Leaf color*.—Young upper surface; 137A to 137B, young lower surface; 138B, mature upper surface; 137A to 137B, mature lower surface; a color between 138B and 146B.

*Leaf size*.—Average of 5.1 cm in length and 6.1 cm in width.

*Leaf quantity*.—Average of 8 per lateral branch.

*Petiole size*.—Average of 11.4 cm in length and 2 mm in diameter.

*Petiole color*.—Upper surface 144B, tinged 175D, base strongly tinged 184C, lower surface 145A.

*Stipules*.—Leafy stipule present at the base of the basal leaves; ovate in shape, apex mucronate, margin entire, base truncate, average of 8 mm in length and 3 mm in width, 143B in color with transparent margins, upper surface is glossy, lower surface is dull.

Flower description:

*Inflorescence type*.—Single, rotate, arranged in pairs of 2.

*Lastingness of flowers*.—About 7 days, self cleaning.

*Flower size*.—Average of 2.9 cm in diameter and 1.0 cm in depth.

*Flower fragrance*.—None.

*Flower number*.—Average of 2 flowers per inflorescence.

*Flower aspect*.—Upright to outward.

*Flower bud size*.—Average of 9 mm in length, up to 4 mm in diameter.

*Flower bud color*.—137C, with darker veins 137B, densely covered with short soft hairs average of 1 mm in length and NN155D in color.

*Flower bud shape*.—Ovate.

*Corolla features*.—Petals are unfused and arranged in a rotate form.

*Petal number*.—5.

*Petal shape*.—Obcordate.

*Petal color*.—When opening upper and lower surface; 76C and changing to a color between 65A and N66D with base 69D and veins 67C, fully open upper surface; N66D with base 69D and veins 69D, fully open lower surface; N66D with base 69D and veins N77D.

*Petal surface*.—Both surfaces dull and slightly velvety.

*Petal margins*.—Entire except for apex.

*Petal apex*.—Lobed (average: two lobes that are rounded to acute).

*Petal base*.—Cuneate.

*Petal size*.—Average of 1.7 cm in length and 1.2 cm in width.

*Calyx form*.—Rotate, cupped.

*Calyx size*.—Average of 6 mm in length and 1.3 cm in diameter.

*Sepal number*.—Average of 5.

*Sepal shape*.—Ovate.

*Sepal margin*.—Entire.

*Sepal size*.—Average of 1 mm length, 3 mm in width.

*Sepal surface*.—Both surfaces dull.

*Sepal arrangement*.—Rotate.

*Sepal apex*.—Mucronate.

*Sepal base*.—Cuneate.

*Sepal color*.—Immature upper surface; 143C, veins 137B, immature lower surface; 137C, veins 137B, mature upper surface; 143A, veins 137B, mature lower surface; 138B, veins 137B.

*Peduncle size*.—Average of 4.8 cm in length and 1 mm in diameter.

*Peduncle strength/aspect*.—Moderate to strong, held at about a 30° (0°=straight on top of lateral branch).

*Peduncle shape*.—Round.

*Peduncle color*.—138B.

*Pedicel size*.—Average of 1.7 cm in length and 0.8 mm in width.

*Pedicel shape*.—Round.

*Pedicel strength/aspect*.—Moderate, lateral flowers are held at an average of 15° (varying between 5°and 30°), straight on top of peduncle=0°.

*Pedicel color*.—Both surfaces 138B to 138C in color.

Reproductive organs:

*Gynoecium.*—1 pistil, about 7 mm in length, 5 stigmas are decurrent and 150C in color, style is about 5 mm in length and 144C in color, ovary is 144A in color.

*Androcoecium.*—10 stamens, anthers are dorsifixed, oblong in shape, 1.5 mm in length, 0.7 mm in width, and 24C to 24D in color, filament is 5 mm in length and 157A in color, pollen is low in quantity and 198D in color.

*Fruit/seeds.*—No fruit or seeds detected to date.

It is claimed:

1. A new and distinct cultivar of *Geranium* plant named 'Bremdream' as herein illustrated and described.

* * * * *